(12) United States Patent
Hyde et al.

(10) Patent No.: US 10,589,040 B1
(45) Date of Patent: Mar. 17, 2020

(54) COLLAPSIBLE, DISPOSABLE MDI SPACER AND METHOD

(71) Applicant: THAYER MEDICAL CORPORATION, Tucson, AZ (US)

(72) Inventors: Joel Hyde, Tucson, AZ (US); James Strickland, Tucson, AZ (US); Jennifer Johnson, Tucson, AZ (US)

(73) Assignee: THAYER MEDICAL CORPORATION, Tucson, AZ (US)

( * ) Notice: Subject to any disclaimer, the term of this patent is extended or adjusted under 35 U.S.C. 154(b) by 0 days.

(21) Appl. No.: 16/368,585

(22) Filed: Mar. 28, 2019

(51) Int. Cl.
*A61M 15/00* (2006.01)

(52) U.S. Cl.
CPC ...... *A61M 15/0088* (2014.02); *A61M 15/009* (2013.01); *A61M 15/0021* (2014.02); *A61M 15/0028* (2013.01)

(58) Field of Classification Search
CPC .............. A61M 15/00; A61M 15/0016; A61M 15/0018; A61M 15/0021; A61M 15/0028; A61M 15/0086; A61M 15/0088; A61M 15/009; A61M 11/00; A61M 11/001; A61M 11/04
See application file for complete search history.

(56) References Cited

U.S. PATENT DOCUMENTS

| | | | |
|---|---|---|---|
| 4,951,661 A | 8/1990 | Sladek | 128/202.27 |
| 4,953,545 A | 9/1990 | McCarty | 128/200.23 |
| D335,175 S | 4/1993 | Sladek | D24/110 |
| D362,500 S | 9/1995 | Cook et al. | D24/110 |
| 5,474,058 A | 12/1995 | Lix | 128/200.18 |
| 6,014,972 A | 1/2000 | Sladek | 128/203.12 |
| 6,039,042 A | 3/2000 | Sladek | 128/200.23 |

(Continued)

FOREIGN PATENT DOCUMENTS

| | | | |
|---|---|---|---|
| CA | 2212642 | 8/1996 | A63B 23/18 |
| CA | 2223518 | 12/1996 | A63B 23/18 |

(Continued)

OTHER PUBLICATIONS

Australian Certificate of Registration of Trademark, No. 1751570 for LiteAire, filed Feb. 10, 2016 (1 pg).

(Continued)

*Primary Examiner* — Joseph D. Boecker
(74) *Attorney, Agent, or Firm* — Hayes Soloway P.C.

(57) ABSTRACT

A medication inhalation apparatus formed of a single, unitary sheet of stock, includes an outer housing, movable between collapsed and expanded states, encompassing a first volume. An inner barrier within the outer housing delineates a second volume. An inhaler opening to the first volume is within a sidewall of the outer housing at a first location. A mouth opening to the second volume is within a sidewall of the outer housing at a second location. A one-way inhalation valve connecting the first volume and the second volume is formed from a sidewall of the inner barrier. A one-way exhalation valve connecting the second volume and the exterior of the outer housing is formed from a sidewall of the outer housing and inner barrier at a third location. In the expanded state, gas flows from the inhaler to the first volume, the first volume to the second volume, and the second volume to a user's mouth.

17 Claims, 7 Drawing Sheets

(56) References Cited

U.S. PATENT DOCUMENTS

| | | | | |
|---|---|---|---|---|
| 6,098,619 A | * | 8/2000 | Britto | A61M 11/003 128/203.12 |
| 6,202,643 B1 | * | 3/2001 | Sladek | A61M 15/0086 128/200.23 |
| 6,435,176 B1 | | 8/2002 | Berg et al. | 128/200.23 |
| 6,550,473 B1 | | 4/2003 | Sladek | 128/200.23 |
| 6,679,252 B2 | * | 1/2004 | Sladek | A61M 15/0086 128/200.22 |
| 7,347,203 B2 | | 3/2008 | Marler et al. | 128/201.13 |
| 7,360,537 B2 | | 4/2008 | Snyder et al. | 128/200.23 |
| 7,921,846 B1 | | 4/2011 | Marler et al. | 128/205.24 |
| 2002/0129814 A1 | | 9/2002 | Sladek | 128/200.23 |
| 2009/0032019 A1 | * | 2/2009 | Green | A61M 15/0086 128/203.29 |
| 2010/0163045 A1 | * | 7/2010 | Powell | A61M 11/00 128/203.29 |
| 2019/0151578 A1 | * | 5/2019 | Dennis | A61M 15/0088 |
| 2019/0231994 A1 | * | 8/2019 | Jaroslavsky | A61M 15/0086 |

FOREIGN PATENT DOCUMENTS

| | | | | |
|---|---|---|---|---|
| EP | 1204437 | 2/2005 | | A61M 11/04 |
| WO | WO 96/37249 | 11/1996 | | A61M 15/00 |
| WO | WO2017205907 | 12/2017 | | A61M 15/00 |
| WO | WO-2019007968 A1 | * 1/2019 | | A61M 15/00 |

OTHER PUBLICATIONS

LiteAire® sales literature, downloaded from http://thayermedical.com on Apr. 18, 2019 (20 pgs).

* cited by examiner

Method of expanding a medication inhalation apparatus from an initially flat, collapsed state

600

610 — Providing, in the collapsed state, an outer housing, an inner barrier positioned within the outer housing, an inhaler opening formed at least partially within a sidewall of the outer housing at a first location, a mouth opening positioned within a sidewall of the outer housing at a second location, a one-way inhalation valve positioned within a sidewall of the inner barrier and formed from the inner barrier, and a one-way exhalation valve positioned within a sidewall of the outer housing and the inner barrier at a third location, wherein the exhalation valve is formed from the outer housing;

620 — Manually pressing a pair of opposite sidewall panels on the outer housing towards one another;

630 — Manually expanding the outer housing and inner barrier to create a first volume encompassed by the outer housing and a second volume delineated by the inner barrier and a mouth opening end of the outer housing, wherein the inhaler opening is in fluid communication with the first volume, wherein the mouth opening is in fluid communication with the second volume, wherein the inhalation valve connects the first volume and the second volume, wherein the exhalation valve connects the and the exterior of the outer housing, and wherein gas is flowable from the metered dose inhaler to the first volume, from the first volume to the second volume and from the second volume to the mouth of a user.

FIG. 6

COLLAPSIBLE, DISPOSABLE MDI SPACER AND METHOD

FIELD OF THE DISCLOSURE

The present disclosure is generally related to aerosol medication inhalers and more particularly is related to valved chambers for delivering aerosol medication from an MDI canister.

BACKGROUND OF THE DISCLOSURE

Pressurized Metered Dose Inhaler (MDI) canisters, which have been used since 1956, ordinarily are sold with a dispenser or so-called "boot" that includes an actuator, a nozzle, and a mouthpiece. The user can self-administer the MDI medicament using the boot alone; however, the user must place the mouthpiece of the boot in or near his/her mouth and inhale at essentially the same time the MDI canister is actuated. Some users, like young children and the elderly, find it difficult to coordinate their inhalation with the actuation of the MDI, and even if the user is able to coordinate their inhalation with MDI inhalation, a lot of medicament is deposited into the oropharynx, leading to undesirable side-effects, such as hoarseness or thrush when using corticosteroids.

At first, "Spacers" were created to address the undesirable oropharyngeal deposition; however, these devices do not address the need for coordinated breathing technique. Medical device manufacturers have since created valved holding chambers (VHCs) to address both issues. To combat oropharyngeal deposition, VHCs (like spacers) have a chamber that holds the aerosol plume. This chamber lets the aerosol plume decelerate giving medicament particles the volume needed to aerosolize, and it allows particles that would normally impact on the user's oropharynx to deposit on the inside of the chamber instead. To help alleviate any issues with the synchronization of a user's breath with MDI actuation, VHCs also employ a valving system that permits the user's inhalation to draw the medicament from the chamber but re-directs the user's exhalation to be vented out of the mouthpiece of the VHC such that the remaining aerosolized medicament inside the chamber is not blown backwards out of the chamber. This allows patients who can't synchronize their inhalation with MDI actuation to get a significant dose of medicament. It also allows the patient to continue breathing through the VHC throughout the treatment, as the presence of the exhalation valve means there is no need to remove the VHC from the patient's mouth during exhalation. Ultimately, the patient can take in the full dose, while breathing as normally as possible, over multiple breaths if necessary. These devices have now become the recommended as the best-practice accessory to an MDI for patients of all ages.

Many commercially available VHCs, like the Aerochamber Plus® Z-Stat® device available from Monaghan Medical Corporation, and Optichamber® Diamond device available from Philips Respironics, are made of rigid plastic and are substantially cylindrical in shape with a diameter of a couple inches and a length of roughly half a foot, which presents problems to users that need to carry MDI canisters with them all day in case of an emergency asthma attack. Also, in facilities that store large numbers of holding chambers, like hospitals or spirometry testing facilities, the cylindrical shape of most VHCs means that the storage of many VHCs takes up a significant amount of space. Some VHC manufacturers have identified these issues and have partially addressed them by creating collapsible cylindrical VHCs. Many of these collapsible VHCs, however, don't offer a significant advantage to a non-collapsible chamber. For example, the BreatheRite™ collapsible device available from Medline Industries, Inc., shortens the length of the device by a couple inches when collapsed, but the device is still a rigid cylinder with the same diameter. The cylindrical shape still means that the device can't fit comfortably in a user's pocket, as well as meaning that storing large quantities of these devices would still take large amounts of space. The Thayer Medical LiteAire® spacer device collapses to a substantially flat configuration and the dimensions of the VHC allow the device to be carried unobtrusively in a shirt pocket or purse. Also, many LiteAire® spacer devices can be stored in a relatively small area because the packaged devices can be stacked flat on top of each other with very little empty space between devices, which is not possible with cylindrically shaped devices like the BreatheRite™ collapsible device.

Conventional VHCs, like the Aerochamber Plus® Z-Stat® device and Optichamber® Diamond device, cost in the range of $10-20. Some medical applications, like spirometry testing, only require a VHC to be used during a brief testing period by a patient, and this price offers a barrier to the use of a VHC in these settings. While lower cost plastic VHCs have recently been introduced to the market, the recent awareness of the need for environmental sustainability identified another problem with the rigid cylindrical plastic solution. Plastic taxes the environment when disposed of with the frequency required in higher-usage clinical environments like spirometry testing facilities. The LiteAire® offers a solution to this problem as well, with 98% of the device being made from paperboard, the environmental impact upon disposal of the device is substantially reduced.

Another benefit of the LiteAire®'s collapsible device construction is that the device is made of a paperboard which is inherently an antistatic material. The fact that the traditional plastic construction of other VHCs creates a large amount of medicament deposition due to static build up on the inside surface of the VHC has been established by multiple sources, including some patents. Multiple patents have been filed for VHCs or spacers made from antistatic materials. For example, U.S. Pat. Nos. 6,435,176 and 7,360,537, which describe devices made from metal and antistatic plastic, respectively, seek to address this problem. These patents offer solutions to electrostatic deposition but run into some of the same rigidity, cost, and disposal problems mentioned above; and they remain bulky and/or expensive. The LiteAire® collapsible device is able to reduce electrostatic deposition as well as being inexpensive, easily portable and environmentally friendly.

While the current LiteAire® collapsible device offers an inexpensive, disposable, collapsible, and antistatic VHC, the current LiteAire® collapsible device employs plastic valves, which creates certain manufacturing challenges. The valves being a different material than paperboard, require a special form of adhesion. Adhesion could come in the form of solvent bonding, heat bonding, pressure bonding, vibration bonding or an actual adhesive, but regardless of the type of adhesion used, related extra steps and expenses in the manufacturing process are required. The replacement of separate plastic valves with valves made from the same sheet material as the rest of the device simplifies not only the manufacturing of the device, but also simplifies the selection of materials and bonding methods available for manufacturing, considering that bonding a material to itself requires less considerations than bonding two potentially dissimilar materials.

In addition to potential time and expense improvements made to the LiteAire® collapsible device manufacturing process, the replacement of the plastic valves with paperboard means that the disposal of the device in an ecologically friendly way, becomes much faster. This means that the replacement of the plastic valves with valves made of the same paperboard material as the body allows the new LiteAire® collapsible device to be made with 100% renewable resources.

The present application addresses these potential variants in the LiteAire® collapsible device design. These variants would continue to provide the same advantages that the current LiteAire® collapsible device already offers over the prior art discussed above and adds additional advantages.

SUMMARY OF THE DISCLOSURE

Accordingly, it is an object of the invention to improve the cost of manufacturing a collapsible/expandable valved chamber device for delivering MDI medications for the like.

It is another object of the invention to provide an inexpensive, disposable, collapsible valved chamber for delivering MDI medications, or other inhaled treatments.

It is another object of the invention to provide an inexpensive, disposable valved chamber which is collapsible to a flat configuration.

It is another object of the invention to provide an easily manufacturable valved chamber which is collapsible to a flat configuration.

It is another object of the invention to provide a valved chamber which is sufficiently inexpensive that it can be used as a discardable diagnostic dosing aid, temporary medication delivery aid, or training aid by means of which a health care provider can demonstrate proper techniques for using a permanent valved chamber.

The present disclosure can be viewed as providing a medication inhalation apparatus. Briefly described, in architecture, one embodiment of the system, among others, can be implemented as follows. The apparatus is formed of a one piece cut and folded stock, includes an outer housing, movable between a collapsed state and an expanded state. The collapsed state has a substantially flat configuration. The expanded state encompasses a first volume. The apparatus also includes an inner barrier positioned within the outer housing, which together with portions of the outer housing, delineates a second volume. A first opening is formed at least partially within a wall of the outer housing at a first location, and adapted to accommodate a mouthpiece of an MDI inhaler, in fluid communication with the first volume. A second opening is positioned within a sidewall of the outer housing at a second location in fluid communication with the second volume. A one-way inhalation valve is positioned within a wall of the inner barrier. The inhalation valve connects the first volume and the second volume. A one-way exhalation valve is positioned within a wall of the outer housing and the inner barrier at a third location. The one-way exhalation valve connects the second volume to the exterior of the outer housing. The inhalation valve and the exhalation valve are both formed integrally with the housing, i.e., as one piece. When the apparatus is in an expanded state, gas is flowable from the metered dose inhaler to the first volume, from the first volume to the second volume, and from the second volume to the mouth of a user.

The present disclosure can also be viewed as providing methods of expanding a medication inhalation apparatus from an initially flat, collapsed state to an expanded state by providing a medication apparatus as above described, and manually pressing a pair of opposite sidewall panels on the outer housing towards one another, whereby to force the opposite sidewall panels into positions approximately perpendicular to top and bottom panels of the outer housing, and inserting a mouthpiece of an MDI inhaler into the mouthpiece opening in the outer housing, whereupon the apparatus is ready for use by a patient.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6 is a flowchart describing a method of expanding a medication inhalation apparatus from an initially flat, collapsed state, in accordance with a first embodiment of the present disclosure.

DETAILED DESCRIPTION

Figure 1:
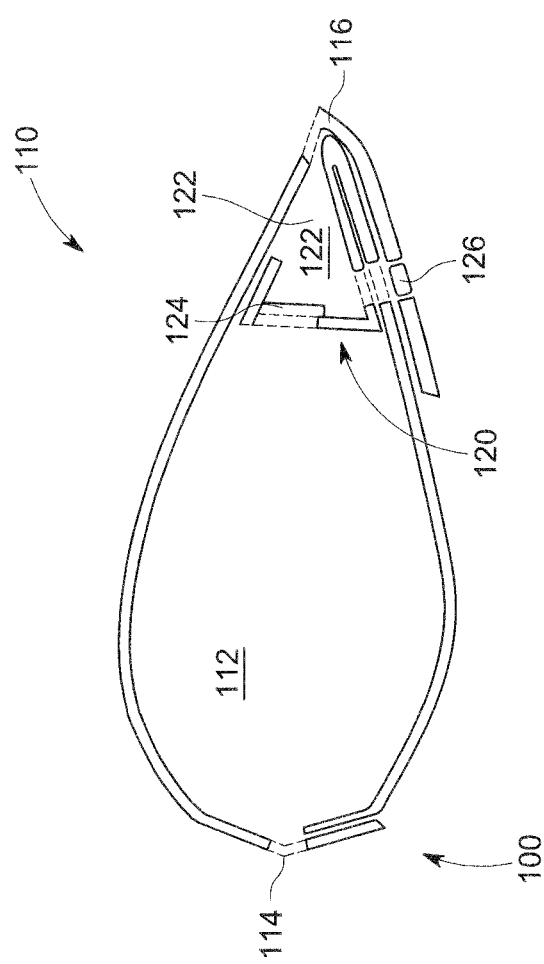
FIG. 1 is a longitudinal cross-sectional view of the apparatus in an expanded state, in accordance with a first exemplary embodiment of the present disclosure.

FIG. 1 is a longitudinal cross-sectional view of the apparatus 100 in an expanded state, in accordance with a first exemplary embodiment of the present disclosure. The apparatus 100 includes an outer housing 110, movable between a collapsed state and an expanded state. The collapsed state has a substantially flat configuration. The expanded state encompasses a first volume 112. The apparatus also includes an inner barrier 120 positioned within the outer housing 110, which, together with the outer housing 110, delineates a second volume 122. A first opening 114 is formed at least partially within a sidewall of the outer housing 110 at a first location, in fluid communication with the first volume 112, and adapted to accommodate the mouthpiece of a metered dose inhaler 77 (see FIG. 4). A second opening 116 is formed within a sidewall of the outer housing 110 at a second location in fluid communication with the second volume 122, and is adapted to form an user mouth opening. A one-way inhalation valve 124 is located on and formed integrally with the inner barrier 120. Inhalation valve 124 connects the first volume 112 and the second volume 122. A one-way exhalation valve 126 is formed within a sidewall of the outer housing 110 and the inner barrier 120 at a third location, and is also formed integrally with the housing. Exhalation valve 126 connects the second volume 122 and the exterior of the outer housing 110. When the apparatus 100 is in an expanded state, gas is flowable from the metered dose inhaler to the first volume 112, from the first volume 112 to the second volume 122, and from the second volume 122 to the mouth of a user. In the expanded state, gas is also flowable from the mouth of a user to the second volume 122 and to the exterior of the outer housing 110.

Figure 2:
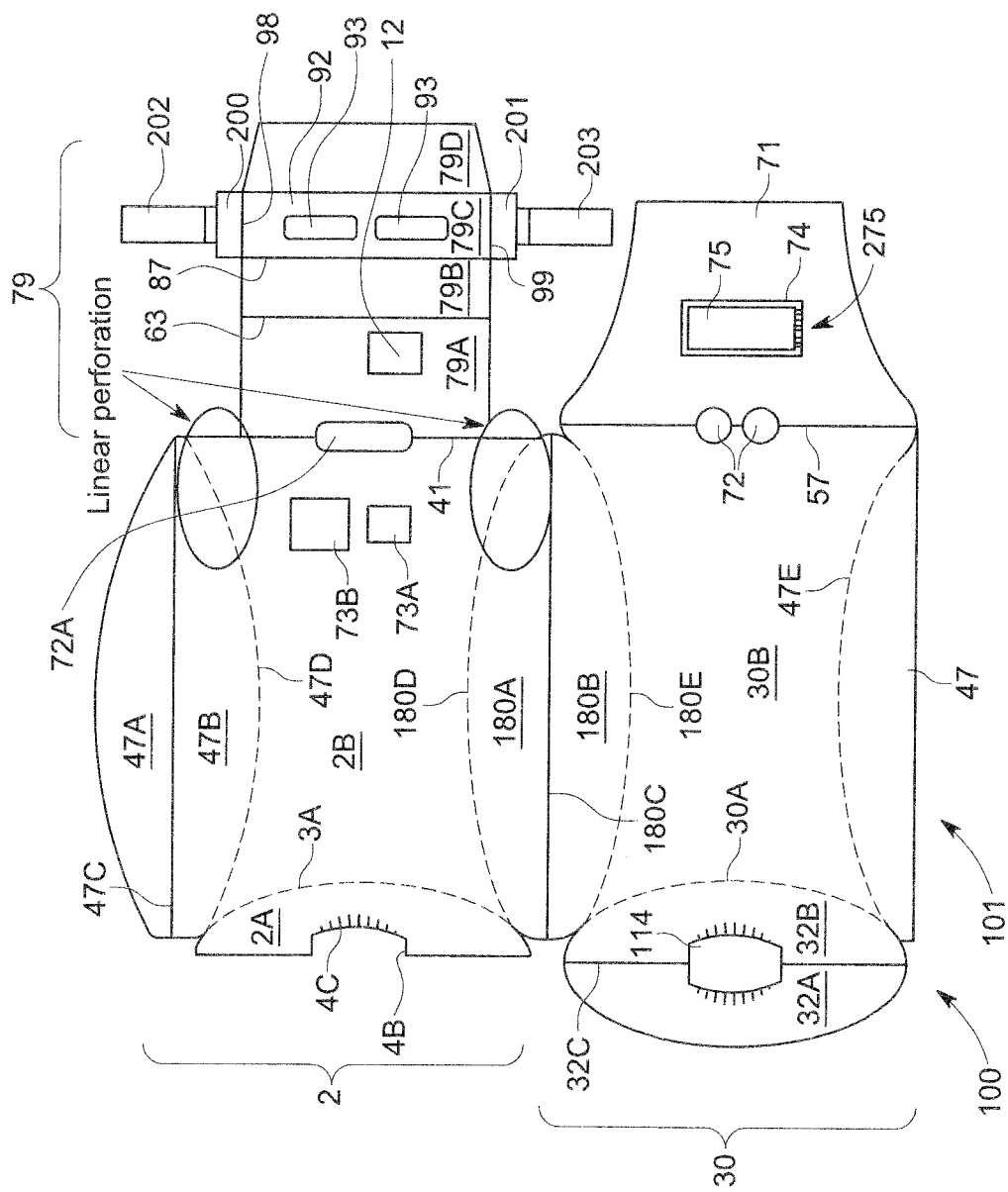
FIG. 2 is an interior plan view of a sheet from which the apparatus is constructed, in accordance with a first exemplary embodiment of the present disclosure.

FIG. 2 is a plan view of a blank or sheet 101 from which the apparatus 100 is constructed, in accordance with a first exemplary embodiment of the present disclosure. The sheet 101, when expanded, takes the shape state shown in FIG. 1. FIG. 2 shows the interior side of the sheet 101, i.e., the side that forms the interior of the apparatus 100 as assembled. Sheet 101 includes a bottom section 2, a top section 30, an inner barrier section 79, and an outer user mouth opening section 71. The inner barrier 120 is formed from the panels in the inner barrier section 79, while the outer housing 110 is formed from the remaining portions of the sheet 101. The bottom section 2 and top section 30 are connected by a side section, which includes two side panels 180A and 180B connected by a straight scored fold line 180C as shown. Side panel 180A is connected along an arcuate "skip-scored" fold line 180D to bottom panel 2B, and side panel 180B is connected along an arcuate skip-scored fold line 180E to top panel 30B. (A skip-scored fold line includes a sequence of scored and non-scored sections of a fold line having the appearance of dashed line.).

On the top section 30, adhesive attachment panel 47 is connected by an arcuate scored fold line 47E to top panel 30B, and eventually is adhesively attached to the inner surface of left side panel 47A on bottom section 2, as will be described below. Side panel 47A is connected to panel 47B, which is connected to bottom panel 2B by arcuate skip-scored fold line 47D.

In one example, skip-scored fold lines 47D, 180D may only be partially arcuate. That is, the portion of the fold lines beginning near inhaler opening 114 may be arcuate, but the portion of the fold lines near the openings 72 may be substantially linear.

On the bottom section 2, an end portion of bottom panel 2B is connected along an arcuate skip-scored fold line 3A to an inner boot adapter panel 2A. Conversely, on the top section 30, an outer boot adapter panel 32A,B includes a panel 32A which is connected along a straight scored fold line 32C to an outer boot adapter panel 32B, which is connected along arcuate skip-scored fold line 30A to an end of top panel 30B. A portion of an elongated inhaler opening 114 bounded by scalloped sections 4B, which are formed by slits 4C, is aligned with a corresponding portion of half-opening 4B in inner boot adapter panel 2A.

User mouth opening section 71 is connected along straight scored fold line 57 to top panel 30B. Circular mouth openings 72 may be symmetrically formed in both top panel 30B and user mouth opening section 71, so as to be bisected by scored fold line 57. However, user mouth openings 72 need not be circular, but may be any suitable shape, such as square, rectangle, oval, and the like. Also, user mouth openings 72 may be located at any suitable point along top panel 30B and user mouth opening section 71. For instance, user mouth openings 72 may be exclusively located on top panel 30B or exclusively located on user mouth opening section 71. Or, user mouth openings 72 may be asymmetrically formed in both top panel 30B and mouthpiece section 71.

A rectangular exhalation valve flap 75 is formed from user mouth opening section 71. In one example, the exhalation valve flap 75 may be cut into about the center of user mouth opening section 71 on three sides, forming a gap 74. On the remaining side, hinge 275 may be cut. This is explained in greater detail with reference to FIG. 3A, below. The exhalation valve flap 75 may be any size and shape suitable for use as an exhalation valve. The exhalation valve flap 75 may be connected to the user mouth opening section 71 by any suitable number and orientation of hinges cut into the sheet 101.

In one example, exhalation valve opening 73A is formed in bottom panel 2B. When the apparatus 100 is assembled, exhalation valve opening 73A enables the second volume 122 to be in fluid communication with the exterior of the apparatus 100 when a user exhales. Hinge recess 73B may be formed near to exhalation valve opening 73A in bottom panel 2B. When the apparatus 100 is assembled, hinge recess 73B enables the exhalation hinge 275 to operate within the opening. This is discussed in greater detail with reference to FIG. 3B, below.

Inner barrier section 79 includes a rectangular panel 79A connected along straight scored fold line 41 to bottom panel 2B and a rectangular panel 79B connected along a straight scored fold line 63 to panel 79A. An opening 12 in panel 79A is adapted to align with exhalation valve opening 73A when panel 79A is folded against the inner surface of bottom panel 2B as shown in FIG. 1. When assembled, the portion of the apparatus 100 wherein opening 72A is located may be the opening side of the apparatus 100.

In one example, an elongated rectangular opening 72A is symmetrically formed in bottom panel 2B and panel 79A so as to be bisected by fold line 41. Opening 72A may be any suitable shape to work in conjunction with openings 72. Opening 72A may comprise one or more openings to work in conjunction with openings 72. Opening 72A may be located at any point on bottom panel 2B or panel 79A to work in conjunction with openings 72. For instance, depending on the location of openings 72, opening 72A may be located entirely on bottom panel 2B, entirely on panel 79A, or asymmetrically formed within both bottom panel 2B and panel 79A. Panel 79B is connected to another panel 79C along a straight scored fold line 87. Rectangular inhalation valve openings 93 are formed in panel 79C. Panel 79C is attached to trapezoidal panel 79D along a straight skip-scored fold line 92. Preferably, inhalation valve openings 93 are as large as can be practically fit into panel 79C while nevertheless providing for proper operation of inhalation valve flaps 202, 203.

Side panels 200 and 201 are connected to panels 79B and 79C along straight, continuously-scored or perforated fold lines 98 and 99. The side panels 200, 201 fold around panel 79C to bring inhalation valve flaps 202, 203 in line with inhalation valve openings 93. When the apparatus is assembled, inhalation valve flaps 202, 203 cover inhalation valve opening 93, allowing fluid communication between the first volume 112 and the second volume 122 when a user inhales. The inhalation valve mechanisms are discussed further in FIGS. 3A-B, below.

It should be noted that all openings may have any size, shape, orientation, number, and placement suitable to work in conjunction with each other and to facilitate use by a user. FIGS. 1 and 2 show exemplary openings generally located centrally on the apparatus 100.

Figure 3A:
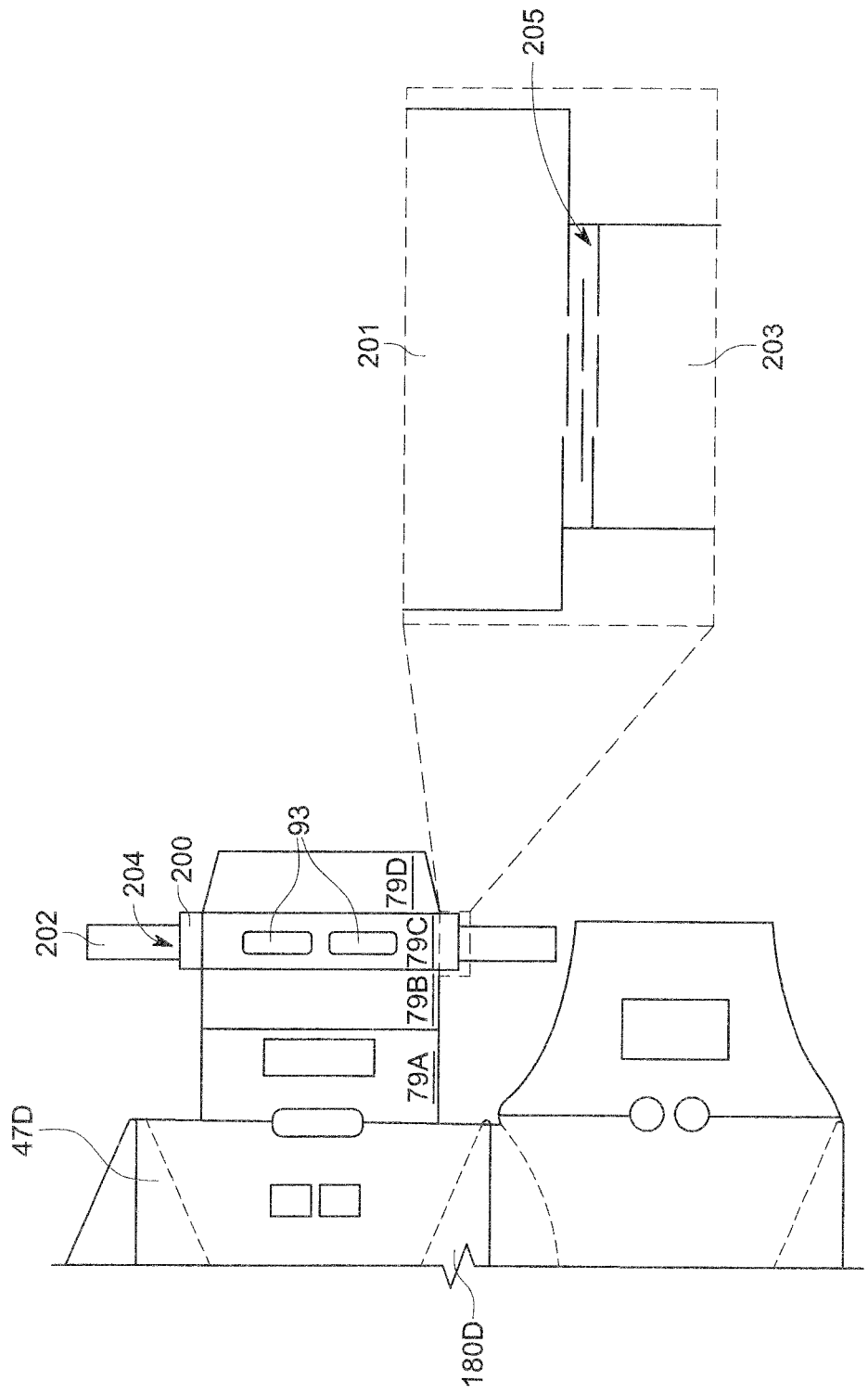
FIG. 3A is a close-up plan view of the sheet of FIG. 2, in accordance with a first exemplary embodiment of the present disclosure.

FIG. 3A is a close-up plan view of the sheet 101 of FIG. 2, in accordance with a first exemplary embodiment of the present disclosure. FIG. 3A shows the portion of the sheet 101 that, when assembled, forms the inner barrier 120 of FIG. 1. Panels 79A-D are shown connected by score lines, as discussed in FIG. 2. Connected to panel 79C are side panels 200 and 201. In the example shown in FIG. 2, side panels 200 and 201 are the same design on opposite sides of side panel 79C.

Side panel 201 is shown within the close-up inset. Side panel 201 comprises a generally rectangular panel connected to a rectangular inhalation valve flap 203 by hinge 205 cut into the panel 201. Hinge 205 comprises a series of skip scored through-cut lines in several rows. FIG. 3A shows 3 rows of lines in a so-called running bond brick pattern. However, any number of rows or any suitable pattern may be used. The pattern cut into the panel 201 allows the hinge portion of the panel 201 to bend flexibly as necessary for operation of the apparatus 100 while still maintaining structural integrity. Additionally, the hinge 205 provides a limited spring action that returns the valve approximately to its neutral or starting position after use. Side panel 200 is constructed the same as side panel 201. Inhalation valve flap 202 is connected to side panel 200 by hinge 204, which is shown as a running bond pattern, but may be any suitable pattern.

Skip scored lines 47D and 180D are shown as linear or straight, rather than arcuate lines in the visible portion of FIG. 3A. When the apparatus 100 is assembled and expanded, the linear lines ensure that the bottom side of the apparatus 100 remains flat, allowing the exhalation valve to remain in contact with the bottom side.

When assembled, the side panels 79A, 79B, 79C, 79D, 200, 201 fold inward to create an inner barrier 120. Inhalation valve flaps 202 and 203 fold inward to cover inhalation valve openings 93. When a user inhales, inhalation valve flaps 202, 203 bend inward to allow gas from the first volume 112 to enter the second volume 122. When a user is not inhaling, or when exhaling, inhalation valve flaps 202, 203 remain substantially sealed against panel 79C to prevent fluid communication of the first volume 112 and second volume 122 through inhalation valve openings 93.

Figure 3B:
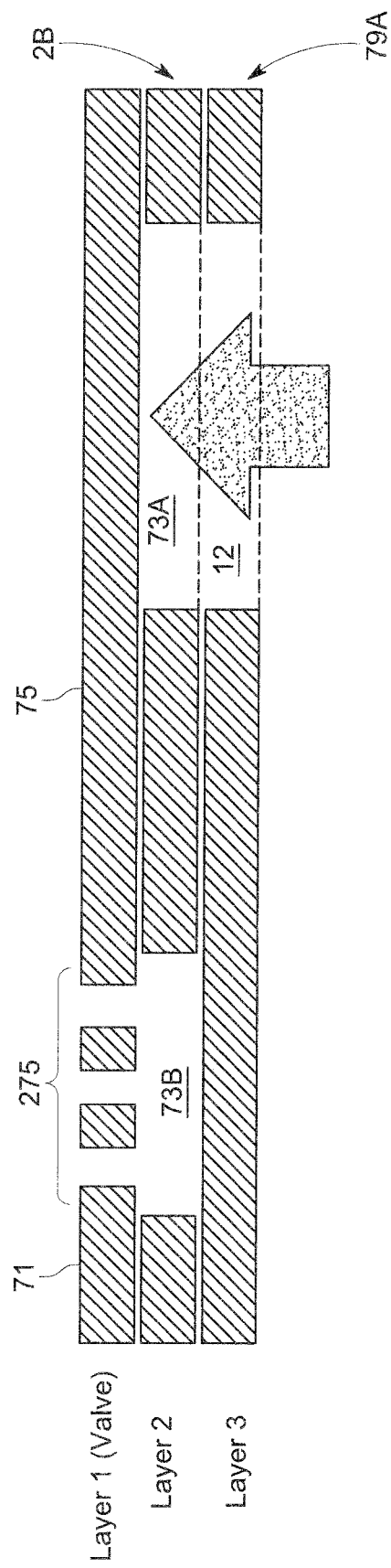
FIG. 3B is a cross-sectional view of a valve and hinge on the apparatus, in accordance with a first exemplary embodiment of the present disclosure.

FIG. 3B is a cross-sectional view of a valve and hinge on the apparatus, in accordance with a first exemplary embodiment of the present disclosure. As an example, FIG. 3B shows the exhalation valve mechanism having 3 layers. The mechanism design may have any suitable number of layers and may be used in the inhalation valve mechanism as well. In the example shown in FIG. 3B, the outermost layer comprises outer mouth opening section 71, connected to valve hinge 275, which is connected to exhalation valve flap 75. This outermost layer is folded against the exterior of bottom panel 2B. While cutting the hinges for the valves, it is possible for excess sheet material to protrude from underneath the valves. In one example, a hinge recess 73B may provide relief space for the hinge 275 and any additional sheet material. This may allow the hinge 275 to maintain the exhalation valve flap 75 flat against the second layer 2B. The third layer comprises panel 79A, which is folded against bottom panel 2B when forming the inner barrier 120.

Opening 12 in panel 79A aligns with exhalation valve opening 73A to provide a channel for fluid communication from one side of the valve flap 75 to the other.

Referring to FIGS. 1-3B, the apparatus 100 may be constructed from the sheet 101 as follows. Reference will be made to the "topside" and "underside" of the panels comprising sheet 101, the "topside" being the portion of the panel or flap visible in FIGS. 2 and 3A, while the "underside" is the opposite side not visible in the drawings.

In one example, the apparatus 100 is cut or punched from a single, unitary sheet 101 of suitable material, such as solid bleached sulfate paperboard, plastic, spun nonwoven polymer such as TYVEK® by DuPont, or the like. The material may be an antistatic or static dissipative paper to reduce static deposition of medicine particles on the walls of the apparatus 100. In one example, the sheet 101 may be coated in a static dissipative coating or the like. Inhalation valves 124 and exhalation valve 126, including valve hinges 204, 205, 275 and valve flaps 202, 203, 75, may be created from the unitary sheet 101 by die cutting, punching, laser cutting, an X-Y table cutter, or a combination thereof. The apparatus 100 may include multiple cutting steps, depending on the accuracy desired for each step. For instance, a steel rule die may not be able to accurately cut out the hinges, so a steel rule die may be used to cut out other portions of the apparatus 100, while a laser cutter may be used for the finer cuts.

The inner barrier 120 may be assembled next. The panels and flaps may be fixed or glued together using one or more suitable adhesives. The folding and gluing process starts by applying adhesive to the bottom side of side panels 200, 201. Side panels 200, 201 are folded over lines 98, 99, respectively, so that the adhesive sides contact the underside of panel 79C. Adhesive is then applied to the topside of panel 79A, which is folded over line 41 so that the adhesive surface contacts the topside of bottom panel 2B. Panel 79B is folded outward along line 63 so that the topside of panel 79B is visible as in FIG. 2. Panel 79C is then folded inward along line 87 so that the topside of panel 79C is not visible. Finally, panel 79D is folded along line 92 so that the topside of panel 79D is visible. Top section 30 is folded over line 180C so that the topside of top panel 30B is in contact with the topside of bottom panel 2B. Adhesive is applied to panel 79D, and it is glued to the topside of top panel 30B.

The outer housing 110 may be assembled next. Adhesive is applied to the topside of panel 32A, which is folded over line 32C and glued to the underside of panel 2A. Adhesive is applied to the topside of panel 47A, which is folded over line 47C and glued to the underside of panel 47. Adhesive is applied to the topside of outer mouth opening section 71, which is folded over line 57 and glued to the underside of bottom panel 2B.

Figure 4:
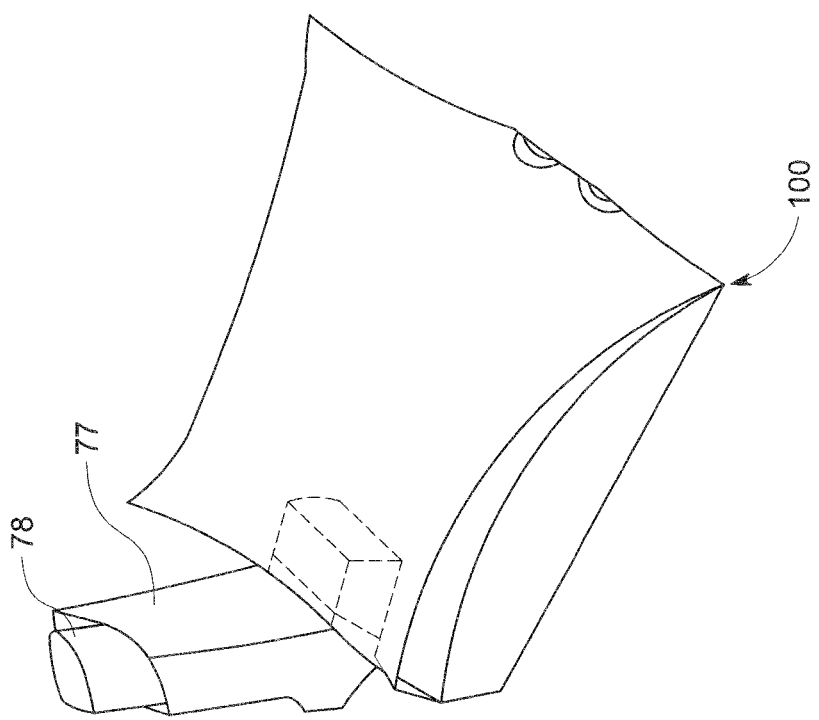
FIG. 4 is a perspective view of the apparatus in an expanded state, in accordance with a first exemplary embodiment of the present disclosure.

FIG. 4 is a perspective view of the apparatus 100 in an expanded state, in accordance with a first exemplary embodiment of the present disclosure. In the expanded state, apparatus 100 is capable of receiving the mouthpiece end of the boot adapter 77 of a conventional inhaler containing an MDI canister 78 inserted through inhaler opening 114 shown in FIG. 1.

Referring to FIGS. 1-4, the apparatus 100 may be expanded as follows. When the apparatus 100 is assembled as described above, it is in its flat or collapsed state. When an user presses right side panels 180A and 180B inward toward left side panels 47A and 47B so that they "unfold" along straight, scored fold lines 180C and 47C, respectively, the apparatus 100 pops into and retains the configuration shown in FIG. 4. The fold lines 63, 87, and 92 allow panels 79B and 79C to be pulled by adhesive and 79D and the rising upper panel 30B upward from their generally horizontal position when apparatus 100 is collapsed so that the panels 79B,C are in a nearly vertical position when apparatus 100 is fully "popped up". Furthermore, as side panels 47A, 47B, 180A, 180B are pressed inward along partially arcuate lines 47D,180D, 47E, 180E they come into contact with the sides of panels 79B,79C, creating delineation between the first volume 112 and the second volume 122 that limits airflow around the sides.

Additionally, when the boot adapter 77 with an MDI canister 78 therein is inserted into opening 114, that causes boot adapter panels 32A and 32B to unfold to the maximum extent.

Figure 5:
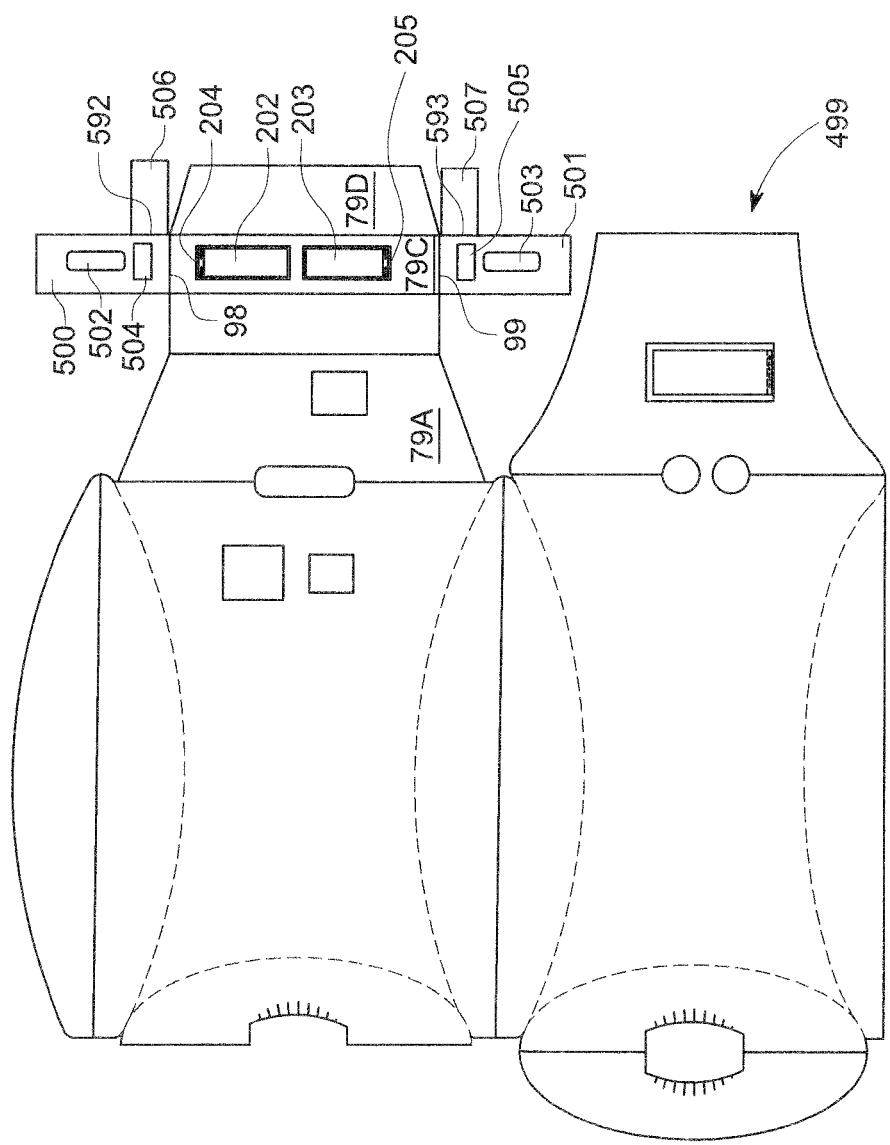
FIG. 5 is a plan view of a sheet from which the apparatus is constructed, in accordance with a second exemplary embodiment of the present disclosure.

FIG. 5 is a plan view of a sheet 499 from which the apparatus 100 is constructed, in accordance with a second exemplary embodiment of the present disclosure. In one example, the design of the sheet 499 may be substantially similar to sheet 101 shown in FIG. 2, with the exception of the inhalation valve design. Instead of the inhalation valve openings 93 located on panel 79C, the inhalation valve flaps 202, 203 and valve hinges 204, 205 are located thereon. Side valve panels 500, 501 are connected to the sides of panel 79C by lines 98 and 99, respectively. Side valve panel 500 comprises valve opening 502, hinge recess 504, and recess flap 506. Side valve panel 501 comprises valve opening 503, hinge recess 505, and recess flap 507. When assembled, side valve panels 500, 501 may be folded so that the topside of side valve panels 500, 501 is in contact with the topside of panel 79C, and the panels 500, 501, 79C may be glued together. This causes valve openings 502, 503 to align with inhalation valve flaps 202, 203 which can open towards a user's mouth to allow gas to flow from the first volume 112 to the second volume 122. Recess flaps 506, 507 may be folded over lines 592, 593 so that the underside of the recess flaps 506, 507 is in contact with the underside of the side valve panels 500, 501, respectively. The recess flaps 506, 507 may be glued to the side valve panels 500, 501. This, along with hinge recesses 504, 505 creates a relief space for the valve hinges 204, 205 to operate, as discussed with respect to FIG. 3B, above.

It is noted that panel 79A is shown as a trapezoid, which better conforms to the shape determined by the partially arcuate fold lines 47A, 47B, 180A, 180B when the apparatus 100 is expanded. Panel 79A may be any suitable shape to achieve an airflow-limiting delineation between the first volume 112 and the second volume 122, and the trapezoidal shape is not limited to any particular embodiment.

FIG. 6 is a flowchart 600 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 610, an expandable apparatus 100 as described above is provided in a collapsed state.

In step 620, a pair of opposite sidewall panels on the outer housing is manually pressed toward one another, causing the outer housing and inner barrier to manually expand to create a first volume encompassed by the outer housing and a second volume delineated by the inner barrier and a mouth opening end of the outer housing (step 630), wherein the inhaler opening is in fluid communication with the first volume, wherein the mouth opening is in fluid communication with the second volume, wherein the inhalation valve connects the first volume and the second volume, and wherein the exhalation valve connects the second volume and the exterior of the outer housing, whereupon gas is flowable from the metered dose inhaler to the first volume, from the first volume to the second volume, and from the second volume to the mouth of a user.

Operating Example

The following operating example may illustrate how the apparatus 100 is used in implementation.

The apparatus 100 may be assembled as described relative to FIGS. 1-3 and 5 above. The outer housing 110 is expanded as described relative to FIG. 4. A user inserts the mouthpiece end of the boot adapter 77 of an inhaler container an MDI canister 78 through the inhaler opening 114 of the apparatus 100 until it fits snugly. The user then places his or her mouth on the mouth opening 116, and exhales into the second volume 122. The user's exhaled breath exits the second volume 122 through the exhalation valve 126. Increased pressure in the second volume 122 causes valve flap 75 to flex away from exhalation valve opening 73A using valve hinge 275, allowing the exhaled breath to escape the apparatus 100. As the user finishes exhaling, the valve flap 75 returns to its "closed" position on the apparatus 100, preventing air from entering the apparatus 100. The user next engages the MDI canister 78 to spray medicine into the first volume 112 of the outer housing 110. The medicine initially expands and fills the first volume 112, as the user inhales through the apparatus 100, causing the inhalation valve 124 to open. Valve flaps 202 and 203 flex open into the second volume 122 of the apparatus, allowing the medicine to travel from the first volume 112 to the second volume 122. As the user continues to inhale, the medicine continues to travel from the second volume 122 into the user's mouth through the mouth opening 116. After the user has finished inhaling, the valve flaps 202, 203 returns to their "closed" position on the inner barrier 120, preventing air from the outer housing 110 from entering the second volume 122.

In some cases, an user may perform some of the steps in a different order. For instance, the user may engage the MDI canister 78 to spray before exhaling, or the user may wait some time between engaging the MDI canister 78 and inhaling. The apparatus 100 is designed to deliver an effective dose even under these conditions.

Test Examples

The following test example may illustrate the effectiveness of the apparatus 100 in creating a medication inhalation apparatus with improved medication delivery.

In evaluating the efficacy of the apparatus of the present invention, two iterations of the apparatus 100 were evaluated against the currently available Thayer Medical LiteAire®, a pop-up, disposable MDI holding chamber as described in U.S. Pat. No. 6,550,473 which had previously improved medication delivery efficacy over the prior art. One difference between the current LiteAire® device and the subject apparatus 100 is that the current LiteAire® device uses bendable membranes glued to the sheet 101 as inhalation and exhalation valves. Therefore, the test will show any differences in efficacy between the unitary valve design and the membrane design. For this experiment, the apparatus 100 was made from 16 point SBS paperboard as described above. A Trudell Fast-Screening Andersen Cascade Impactor (T-FSA) was used to measure total emitted dose (TED), coarse particle dose (CPD) and fine particle dose (FPD) delivered by both devices. The particle size distributions of the two devices were compared with both coordinated and uncoordinated breathing as well as constant inhalation. Coordinated breathing is defined as actuation of the MDI occurring during the onset of user inhalation. Uncoordinated breathing is defined as actuation of the MDI occurring during the onset of user exhalation. Constant inhalation is where the machine is simply run continuously. A good metric of the efficacy of the apparatus 100 to mitigate user incoordination is the amount of dose lost from the coordinated breathing test to the uncoordinated breathing test.

The subject apparatus 100 performed statistically better than the current LiteAire® device in total emitted dose for constant inhalation and coordinated breathing, as well as fine particle dose for constant inhalation. For coarse particle dose, coarse particle fraction, and fine particle fraction, the results were not statistically different on any of the breathing simulations, and the subject apparatus 100 did not perform statistically worse than the current LiteAire® device for any attribute.

These data seem to indicate that the subject apparatus 100 as a whole performs comparably to the current LiteAire® device, and yet is simpler, has the capability to incorporate alternative sheet material that allow it or be less costly to manufacture, or less costly to dispose or potentially more durable. It should be noted that the design for the subject apparatus 100 also differs from the current LiteAire® device in the placement of the inner barrier 120, which is placed nearer to the mouthpiece end of the outer housing 110. In order to isolate the inner barrier 120 as the cause for this improvement, a modified version of the current LiteAire® was created that placed the inner barrier the same distance away from the mouth opening as in the subject apparatus 100. The tests were again run. The modified LiteAire® device performed slightly better than the subject apparatus 100, indicating that the placement of the inner barrier 120 has a positive effect on overall device efficacy.

However, the tests confirm that the subject apparatus 100 on the whole performs comparably to the current LiteAire® device, despite the subject apparatus 100 being made from a single, unitary sheet, including the valves. Thus, the valve design is robust enough to perform comparably to the current LiteAire® and while offering a range of other desirable characteristics.

Thus, the invention provides a disposable "pop up", valved apparatus 100 which also allows for natural inhalation and exhalation by a user. The described valved apparatus 100 can be maintained in a collapsed, flat configuration, suitable for storage in a suit coat pocket or a briefcase, and expanded immediately prior to use, after which it can be discarded or collapsed for later use by the same user. The described apparatus 100 may be used by health care workers to demonstrate its use to users needing to receive an aerosol medication from an MDI inhaler. The apparatus 100 also is well suited for use in hospital emergency rooms, health-care clinics, pulmonary function labs, or infirmaries. In addition, its portability and low cost make it ideal for use by relief or world health organizations, especially when aerosol vaccines become available.

While the invention has been described with reference to several particular embodiments thereof, those skilled in the art will be able to make the various modifications to the described embodiments of the invention without departing from the true spirit and scope of the invention. It should be emphasized that the above-described embodiments of the present disclosure, particularly, any "preferred" embodiments, are merely possible examples of implementations, merely set forth for a clear understanding of the principles of the disclosure. It is intended that all elements or steps which are insubstantially different or perform substantially the same function in substantially the same way to achieve the same result as what is claimed are within the scope of the invention. For example, an exhalation valve or other port may be provided on any portion of the inner barrier/outer housing. Various other ways of folding the sheet material to achieve the collapsed/expanded configurations can be provided. Different arrangements of lock tabs and lock tab receiving slots than disclosed herein could be provided, or Velcro or similar attachment materials could be used. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medication inhalation apparatus, comprising:
an outer housing, movable between a collapsed state and an expanded state, wherein the collapsed state has a substantially flat configuration, and wherein the expanded state encompasses a first volume;
an inner barrier positioned within the outer housing and, together with a mouth opening end of the outer housing, delineating a second volume;
an inhaler opening formed at least partially within a wall of the outer housing at a first location, the inhaler opening in fluid communication with the first volume, wherein a mouth opening of a metered dose inhaler is insertable therein;
a mouth opening positioned within a wall of the outer housing at a second location, the mouth opening in fluid communication with the second volume;
a one-way inhalation valve positioned within a wall of the inner barrier and connecting the first volume and the second volume, wherein the inhalation valve is formed from the inner barrier; and
a one-way exhalation valve positioned within a wall of the outer housing and the inner barrier at a third location, the exhalation valve connecting the second volume and the exterior of the outer housing, wherein the exhalation valve is formed from the outer housing,
wherein the inhalation valve comprises at least one flap connected to the inner barrier by at least a first hinge, and wherein the exhalation valve comprises at least one flap connected to the outer housing by at least a second hinge;
wherein the at least first and second hinges sit over at least first and second hinge recesses, respectively;
wherein, in the expanded state, gas is flowable from the metered dose inhaler to the first volume, from the first volume to the second volume, and from the second volume to the mouth of a user, and
wherein the apparatus is formed from a single, unitary sheet of stock.

2. The apparatus of claim 1 constructed from a single, unitary sheet of paperboard.

3. The apparatus of claim 2, wherein the outer housing and the inner barrier are formed by punching or cutting and folding the sheet of paperboard.

4. The apparatus of claim 1, wherein the apparatus is at least partially constructed from antistatic sheet stock.

5. The apparatus of claim 1, wherein the inhalation valve and exhalation valve are collapsible to a substantially flat configuration.

6. The apparatus of claim 1, wherein the inhalation valve and exhalation valve are operable by a user's inhaling and exhaling.

7. The apparatus of claim 1, wherein a bottom side of the mouth opening end of the outer housing is substantially flat.

8. The apparatus of claim 7, further comprising at least 2 scored or perforated fold lines along the bottom side of the mouth opening end, wherein the at least 2 scored or perforated fold lines are substantially linear at the mouth opening end of the outer housing and arcuate thereafter along the outer housing.

9. A method of expanding the medication inhalation apparatus of claim 1 from an initially flat, collapsed state, to an expanded state comprising the steps of:
manually pressing a pair of opposite sidewall panels on the outer housing towards one another, whereby to force the opposite sidewall panels into positions approximately perpendicular to a top and bottom panel of the outer housing; and
inserting a mouthpiece of an MDI inhaler into the inhaler opening in the outer housing.

10. A medication inhalation apparatus, comprising:
an outer housing, movable between a collapsed state and an expanded state, wherein the collapsed state has a substantially flat configuration, and wherein the expanded state encompasses a first volume;
an inner barrier positioned within the outer housing and, together with a mouth opening end of the outer housing, delineating a second volume;
an inhaler opening formed at least partially within a wall of the outer housing at a first location, the inhaler opening in fluid communication with the first volume, wherein a mouth opening of a metered dose inhaler is insertable therein;
a mouth opening positioned within a wall of the outer housing at a second location, the mouth opening in fluid communication with the second volume;
wherein a bottom side of the mouth opening end of the outer housing is substantially flat;
said apparatus further comprising at least 2 scored or perforated fold lines along the bottom side of the mouth opening end, wherein the at least 2 scored or perforated fold lines along the outer housing;
a one-way inhalation valve positioned within a wall of the inner barrier and connecting the first volume and the second volume, wherein the inhalation valve is formed from the inner barrier; and
a one-way exhalation valve positioned within a wall of the outer housing and the inner barrier at a third location, the exhalation valve connecting the second volume and the exterior of the outer housing, wherein the exhalation valve is formed from the outer housing,
wherein, in the expanded state, gas is flowable from the metered dose inhaler to the first volume, from the first volume to the second volume, and from the second volume to the mouth of a user,
wherein the apparatus is formed from a single, unitary sheet of stock.

11. The apparatus of claim 10 constructed from a single, unitary sheet of paperboard.

12. The apparatus of claim 11, wherein the outer housing and the inner barrier are formed by punching or cutting and folding the sheet of paperboard.

13. The apparatus of claim 10, wherein the apparatus is at least partially constructed from antistatic sheet stock.

14. The apparatus of claim 10, wherein the inhalation valve and exhalation valve are collapsible to a substantially flat configuration.

15. The apparatus of claim 10, wherein the inhalation valve comprises at least one flap connected to the inner barrier by at least a first hinge, and wherein the exhalation valve comprises at least one flap connected to the outer housing by at least a second hinge.

16. The apparatus of claim 10, wherein the inhalation valve and exhalation valve are operable by a user's inhaling and exhaling.

17. A method of expanding the medication inhalation apparatus of claim 10 from an initially flat, collapsed state, to an expanded state comprising the steps of:
manually pressing a pair of opposite sidewall panels on the outer housing towards one another, whereby to force the opposite sidewall panels into positions approximately perpendicular to a top and bottom panel of the outer housing; and
inserting a mouthpiece of an MDI inhaler into the inhaler opening in the outer housing.

* * * * *